United States Patent [19]

Katsoyannis et al.

[11] Patent Number: 4,992,418
[45] Date of Patent: Feb. 12, 1991

[54] SUPERACTIVE HUMAN INSULIN ANALOGUE-[10-ASPARTIC ACID-B]HUMAN INSULIN

[75] Inventors: Panayotis G. Katsoyannis, Manhasset; Gerald P. Schwartz, Washingtonville, both of N.Y.

[73] Assignee: Mount Sinai School of Medicine, New York, N.Y.

[21] Appl. No.: 74,558

[22] Filed: Jul. 17, 1987

[51] Int. Cl.$^5$ .................. C07K 7/40; A61K 37/02
[52] U.S. Cl. .................... 514/3; 514/866; 530/303
[58] Field of Search ............... 530/303; 514/3, 866

[56] References Cited

U.S. PATENT DOCUMENTS

| | | | |
|---|---|---|---|
| 3,420,810 | 1/1969 | Katsoyannis et al. | 530/303 |
| 3,883,496 | 5/1975 | Geiger | 530/303 |
| 3,883,500 | 5/1975 | Geiger | 530/303 |
| 4,421,685 | 12/1983 | Chance et al. | 530/303 |
| 4,430,266 | 2/1984 | Frank et al. | 530/303 |
| 4,459,226 | 7/1984 | Grimes et al. | 530/303 |
| 4,526,938 | 7/1985 | Churchill | 525/154 |
| 4,569,791 | 2/1986 | Frank et al. | 530/303 |
| 4,569,792 | 2/1986 | Frank et al. | 530/303 |
| 4,581,165 | 8/1986 | Frank et al. | 530/303 |
| 4,652,547 | 3/1987 | Chance et al. | 514/4 |
| 4,652,548 | 3/1987 | Chance et al. | 514/4 |

FOREIGN PATENT DOCUMENTS 0214826 3/1987 European Pat. Off. .

OTHER PUBLICATIONS

Pontiroli, *British Medical Journal*, 284, 303-306 (1982).
Botstein, D. and Shortle, D., Strategies and Applications of in Vitro Mutagenesis, Science, vol. 229, pp. 1193-1201, 1985.
Blake, J. and Li, C. H., Total Synthesis of Human β-Lipotropin, Proc. Natl. Acad. Sci. U.S.A. 80, pp. 1556-1559, 1986.
Erickson, B. W. and Merrifield, R. B., Solid-Phase Peptide Synthesis, Academic Press, vol. II, 3rd Edition, pp. 256-527 (1976).

Smith, Michael, In Vitro Mutagenesis, Annual Review of Genetics, vol. 19, pp. 423-462, 1985.
Chance, R. E., Hoffman, J. A., Kroeff, F. P., Johnson, M. G., Schirmer, E. W., and Bromer, W. W., The Lilly Research Labs., Ind. Ross, M. J. and Wetzei, R., Genentech, Inc., S.F., Pept., Proc. Amer. Pept. Symp. 7th., pp. 721-728, 1981.
Katsoyannis, P. G., Tometsko, A. and Zalut, C., Insulin Peptides. XII, Human Insulin Generation by Combination of Synthetic A & B Chains, Journal of the American Chemical Society, 88, 166, 1966.

(List continued on next page.)

Primary Examiner—F. T. Moezie
Attorney, Agent, or Firm—Brumbaugh, Graves, Donohue & Raymond

[57] ABSTRACT

A superactive insulin analogue of the formula

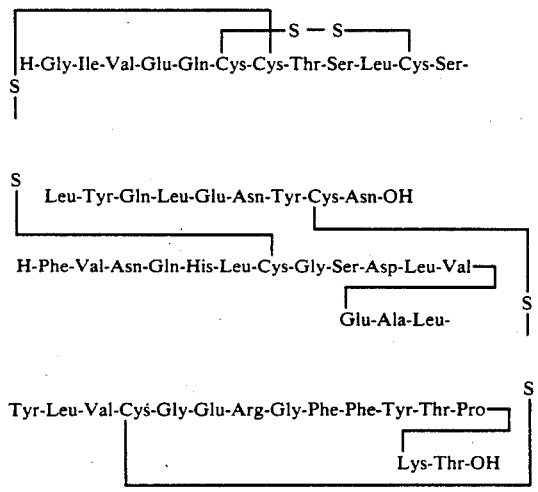

is provided. This analogue is used in therapeutically effective amounts in the preparation of pharmaceutical compositions for administration to diabetic patients.

7 Claims, 2 Drawing Sheets

OTHER PUBLICATIONS

Kitagawa, K., Ogawa, H., Burke, G. T., Chanley, J. D., and Katsoyannis, P. G., Critical Role of the $A^2$ Amino Acid Residue in the Biological Activity of Insulin: [2—Glycine-A]- and [2-Alanine-A]insulins, Biochemistry, 23, pp. 1405–1413, 1984.

Schwartz, G. P., Burke, G. T. and Katsoyannis, P. G., [12-Asparagine-B] Human Insulin—An Analogue with Modification in the Hydrophobic Core of Insulin, Int. J. Peptide Protein Res. 17, pp. 243–255, 1981.

Katsoyannis, P. G. and Tometsko, A., Insulin Synthesis by Recombination of A and B Chains: A Highly Efficient Method, Proceedings of the Natl. Acad. of Sciences, vol. 55, No. 6, pp. 1554–1561, 1966.

Schwartz, G. P. and Katsoyannis, P. G., Insulin Peptides. Part XXIII. The Syntheses of a Hexadecapeptide Derivative Related to the B Chain of Human Insulin, Journal of the Chemical Society, Perkins Transactions I, 1973.

Schwartz, G. P. and Katsoyannis, P. G., Insulin Peptides. Part XXIV. A Novel Synthesis of the Human Insulin B Chain S-Sulphonate, Journal of the Chemical Society, Perkin Transactions I, 1973.

Chan, S. J., Seino, S., Gruppuso, P. A., Schwartz, R., Steiner, D. F., A Mutation in the B Chain Coding Region is Associated with Impaired Proinsulin Conversion in a Family with Hyperproinsulinemia, Proc. Natl. Acad. Sci. U.S.A., vol. 84, pp. 2194–2197, 1987.

Katsoyannis, P. G., Tometsko, A., Zalut, C., Johnson, S. and Trakatellis, A. C., Studies on the Synthesis of Insulin from Natural and Synthetic A and B Chains. I. Splitting of Insulin and Isolation of the S-Sulfonated Derivatives of the A and B Chains, Biochemistry, v, pp. 2635–2642, 1967.

Katsoyannis, P. G., Trakatellis, A. C., Johnson, S., Zalut, C. and Schwartz, G., Studies on the Synthesis of Insulin from Natural and Synthetic A and B Chains. II. Isolation of Insulin from Recombination Mixtures of Natural A and B Chains, Biochemistry, 6, pp. 2642–2655, 1967.

Katsoyannis, P. G., Trakatellis, A. C., Zalut, C., Johnson, S., Tometski, A., Schwartz, G., and Ginos, J., Studies on the Synthesis of Insulin from Natural and Synthetic A and B Chains. III. Synthetic Insulins, Biochemistry, v, pp. 2656–2668, 1967.

Schwartz, G. and Katsoyannis, P. G., Synthesis of Human [9-Leucine-B]Insulin, Biochemistry, 15, pp. 4071–4076, 1976.

Schwartz et al., J. Chem. Research (M), The Synthesis of [10-Leucine-B] Human Insulin, A Biologically Active Analogue, pp. 2453–2466, 1977.

Schwartz, G. P. and Katsoyannis, P. G., The Synthesis of [10-Leuicine-B] Human Insulin, a Biologically Active Analogue, Journal of Chem. Res. (S), pp. 220–221, 1977.

Katsoyannis, P. G., Structure and Function Relationships in Insulin: A Synthetic Approach, Elsevier North Holland, Inc., pp. 171–192, 1980.

Katsoyannis, P. G., New Synthetic Insulins, Treatment of Early Diabetes, pp. 319–328, 1979.

Burke, G. T., Schwartz, G. and Katsoyannis, P. G. Nature of the $B^{10}$ Amino Acid Residue, Int. J. Peptide Protein Res., 23, pp. 394–401, 1984.

Schwartz, G., Burke, G. T., and Katsoyannis, P. G., The Importance of the $B^{10}$ Amino Acid Residue to the Biological Activity of Insulin. [$Lys^{10}$-B] Human Insulin, Journal of Protein Chemistry, vol. 1, No. 3, pp. 177–189, 1982.

Ferderigos, N., Cosmatos, A., Ferderigos, A. and Katsoyannis, P. G., [21-Arginine-A] Insulin—A Biologically Active Analog, Int. J. Peptide Protein Res. 13, pp. 43–53, 1979.

Cosmatos, A., Ferderigos, N., and Katsoyannis, P. G., Chemical Synthesis of [Des(Tetrapeptide $B^{27-30}$), $TYR(NH_2)^{26}$-B] and [DES(Pentapeptide $B^{26-30}$), $PHE(NH_2)^{25}$-B] Bovine Insulins, Int. J. Peptide Protein Res. 14, pp. 457–471, 1979.

Schwartz, G. and Katsoyannis, P. G., Synthesis of Des(tetrapeptide $B^{1-4}$) and Des(pentapeptide $B^{1-5}$) Human Insulins. Two Biologically Active Analogues, Biochemistry, 17, pp. 4550–4556, 1978.

Ferderigos, N., Burke, G. T., Kitawaga, K., and Katsoyannis, P. G., The Effect of Modifications of the $A^5$ and $A^{19}$ Amino Acid Residues on the Biological Activity of Insulin. [$Leu^5$-A] and [$Phe^{19}$-A] Sheep Insulins, Journal of Protein Chemistry, vol. 2, pp. 147–170, 1983.

Schwartz, G., Burke, G. T., Chanley, J. D., and Katsoyannis, P. G., An Insulin Analogue Possessing Higher in Vitro Biological Activity than Receptor Binding Affinity. [21-Proline-B]Insulin, Biochemistry, vol. 22, pp. 4561–4567, 1983.

Kitagawa, K., Ogawa, H., Burke, G. T., Chanley, J. D., and Katsoyannis, P. G., Critical Role of the $A^2$ Amino Acid Residue in the Biological Activity of Insulin: [2—Glycine-A]—and [2-Alanine-A]Insulins, Biochemistry, vol. 23, pp. 1405–1413, 1984.

Kitagawa, K., Ogawa, H., Burke, G. T., Chanley, J. D., and Katsoyannis, P. G., Interaction between the $A^2$ and $A^{19}$ Amino Acid Residues is of Critical Importance for High Biological Activity in Insulin: [19-Leucine-A]insulin, Biochemistry, vol. 23, pp. 4444–4448, 1984.

Proc. Natl. Acad. Sci, U.S., vol. 84, Sep. 1987 (U.S.), G. P. Schwartz et al.: "A Superactive Insulin": [B10-Aspartic Acid] Insulin (Human), pp. 6408–6411.

Chemical Abstracts, vol. 105, 1986, M. Bajaj et al.: "Coypu Insulin. Primary Structure, Conformation and Biological Properties of a Hystricomorph Rodent Insulin", see p. 87, Abstract No. 184142p.

Chemical Abstracts, vol. 101, 1984, G. T. Burke et al.: "Nature of the $B^{10}$ Amino Acid Residue. Requirements for High Biological Activity of Insulin", see p. 72, Abstract No. 84120d.

Chemical Abstracts, vol. 97, 1982, see p. 909, Abstract No. 216734t & DD, A, 153829 (G. Losse et al.) Feb. 3, 1982.

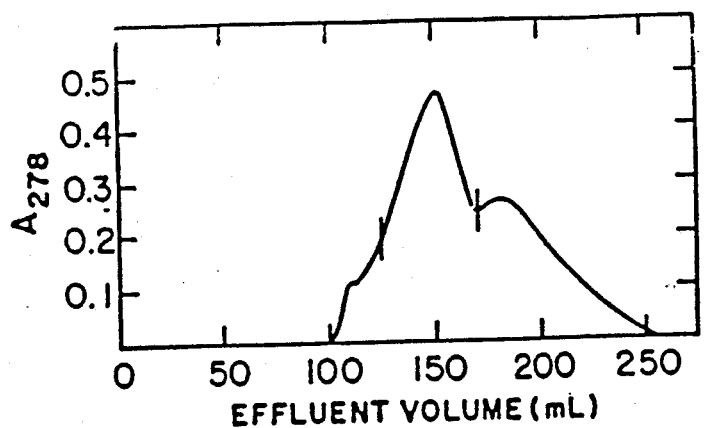
FIG. 1
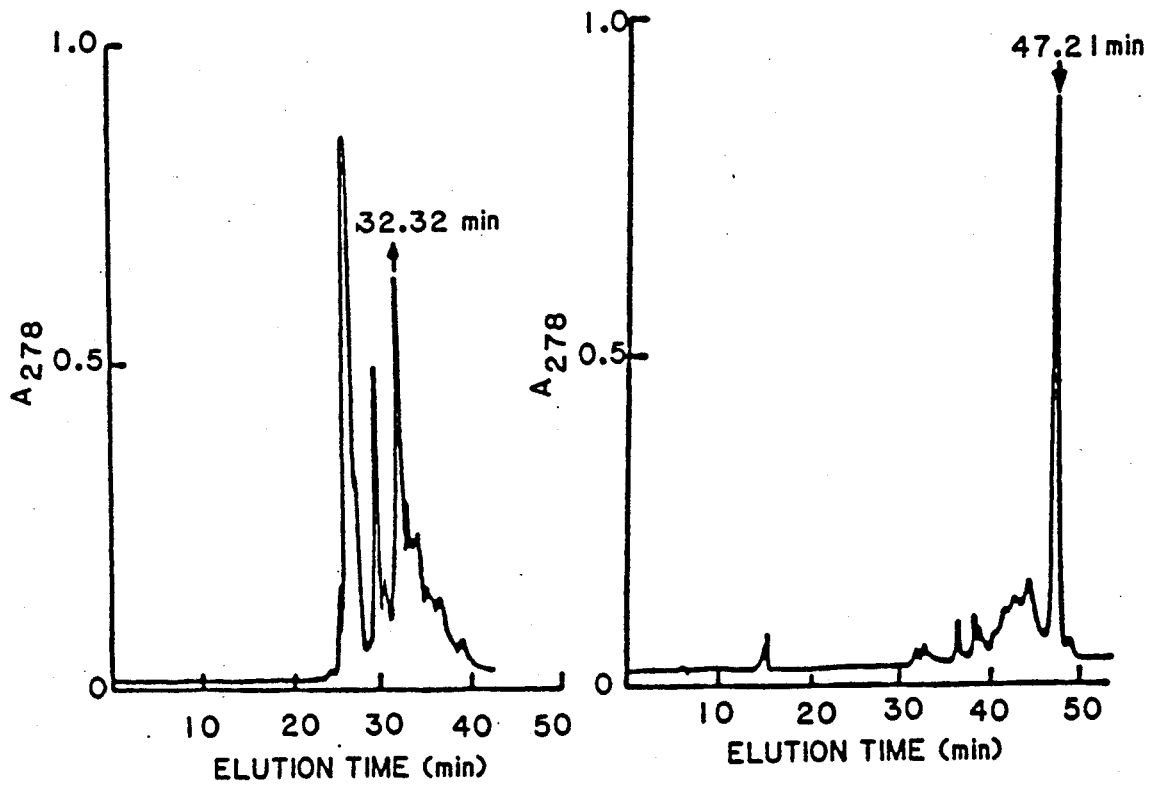
FIG. 2a
FIG. 2b

SUPERACTIVE HUMAN INSULIN ANALOGUE-[10-ASPARTIC ACID-B]HUMAN INSULIN

BACKGROUND OF THE INVENTION

The present invention relates to a novel superactive insulin analogue and its use in pharmaceutical compositions for the treatment of diabetes.

Insulin is a hormone which has a key role in the regulation of growth and metabolism in vertebrates. Severe metabolic derangements occur in the absence of insulin resulting from the failure of many cells to utilize glucose and amino acids normally. The inability to metabolize glucose leads in man to diabetes mellitus, a complex chronic metabolic disorder in which there is abnormal carbohydrate, fat and protein metabolism. In its most fully expressed clinical form, diabetes mellitus is characterized by an absolute or relative deficiency of insulin or insulin activity and is associated with glucosuria, ketonuria, growth arrest, and negative nitrogen balance. These conditions can ultimately lead to death from acute metabolic acidosis caused by unrestrained oxidation of fatty acids or inanition which results from the lack of sufficient lipid reserves needed to generate ketone bodies. Inanition is defined as a condition characterized by marked weakness, extreme weight loss, and a decrease in metabolism resulting from prolonged and severe insufficiency of food. *Dorland's Illustrated Medical Dictionary*, 25th Edition.

The discovery and purification of insulin in the 1920's and its association with diabetes mellitus provided the means to intervene in the disease. See, e.g., Bliss, *The Discovery of Insulin* (1983), University of Chicago Press, Chicago, Ill. Today, insulin administration to diabetic patients is the primary therapeutic means for controlling the disease.

Insulin is a 6000 dalton polypeptide which is composed of two short peptide chains, termed A and B, which are linked to each other by invariant disulfide bridges. In almost all insulins studied, the A chain, which is 21 amino acids long, also contains an internal disulfide bridge. The B chain is 30 amino acids in length. Like many eukaryotic proteins, insulin is synthesized in a precursor form which is post-synthetically processed to the mature two polypeptide chain active hormone.

The immediate precursor of insulin is proinsulin, a single chain polypeptide composed of the B and A chains linked to a connecting peptide of approximately 31 amino acids, termed the C-peptide, by adjacent pairs of basic residues. The order of the three peptides in the proinsulin molecule is $NH_2$-B chain-Arg-Arg-C-peptide-Lys-Arg-A chain-COOH. The translation product of insulin mRNA, however, is preproinsulin which is proinsulin that contains at its $NH_2$ terminus a 24 amino acid largely hydrophobic signal peptide characteristic of proteins that are either transported through or inserted into cellular membranes.

Preproinsulin is synthesized in pancreatic beta cells located within the islets of Langerhans which are dispersed throughout the pancreas. Removal of the signal peptide occurs in the rough endoplasmic reticulum with the resulting fully folded oxidized proinsulin being transported to the Golgi apparatus for packaging into secretion granules. The folded proinsulin is stabilized by disulfide bonds. During maturation of the secretion granules, the folded proinsulin molecule is cleaved by specific proteases at the paired basic residues to liberate insulin and the C-peptide.

As discussed above, therapy for diabetes mellitus includes administration of controlled amounts of insulin to the diabetic patient. The insulin so administered has, for the most part, been obtained from animal pancreases, notably bovine and porcine. Bovine and porcine insulins function to maintain hormonal homeostasis in the same way as human insulin with about the same potency but, because they are foreign proteins, can elicit an immunological response which diminishes their usefulness. More recently, human insulin, generated by recombinant DNA techniques, has been added to the therapeutic armamentarium. The use of human insulin, produced by recombinant DNA or other techniques, is not likely to produce the adverse immunological problems attendant the use of animal insulins. Even with the availability of natural human insulin, however, administration of the hormone to diabetics has not been always sufficient to restore normal metabolism. There is thus a need for alternative insulins with better activity or other means of therapy for diabetes.

Familial hyperproinsulinemia is a genetic disorder characterized by a marked increase in serum proinsulin-like molecules. Three families with this rare disorder have been identified. In two of the families a structurally abnormal proinsulin-like molecule was seen. The genetic defect was identified as a mutation causing an amino acid substitution in proinsulin which results in incomplete cleavage of proinsulin by the proteases which form insulin.

The affected members of the third family produced a proinsulin-like molecule of about the same size as proinsulin that behaved like the normal prohormone in receptor binding assays. Sequence analysis of cloned insulin genes obtained from two affected members from this third family revealed a single coding mutation which substituted an aspartic acid for histidine in the proinsulin molecule at a position which corresponds to position 10 of the B chain of insulin. Chan et al., Proc. Natl. Acad. Sci. (1987), vol. 84, pp. 2194–2197. The mutation was believed to inhibit further processing of proinsulin to insulin, thus resulting in the accumulation of the mutant proinsulin. The precise way the mutation inhibits further processing is not currently known.

A human insulin analogue, [10-Aspartic acid-B] human insulin, which corresponds to this mutant proinsulin, has now been synthesized and has been shown to have greater potency than natural insulins.

SUMMARY OF THE INVENTION

In accordance with the present invention, a superactive insulin analogue, [10-Aspartic acid-B] human insulin having the formula

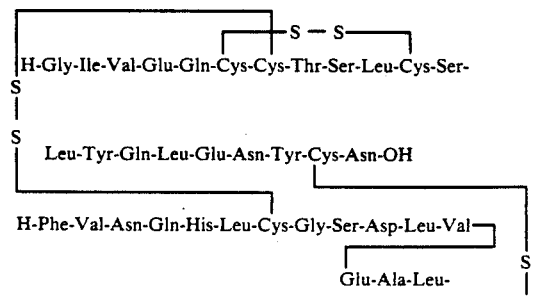

-continued

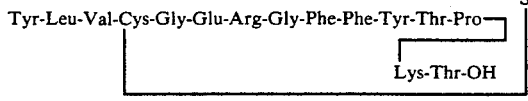

is provided. This insulin analogue demonstrates significantly greater potency than natural human insulin which has histidine at position 10 of the B chain.

The invention also relates to pharmaceutical compositions for the treatment of diabetes in patients needing such treatment which comprise a therapeutically effective amount of [10-Aspartic acid-B] human insulin together with a pharmaceutically acceptable carrier.

Furthermore, the invention relates to a method for treating diabetes comprising adminstering to a diabetic patient in need of insulin therapy a therapeutically effective amount of [10-Aspartic acid-B] human insulin together with a pharmaceutically acceptable carrier.

BRIEF DESCRIPTION OF THE DRAWINGS

FIG. 1 is a chromatogram showing the elution of crude human [10-Aspartic acid] B chain S-sulfonate from a CM-cellulose column.

FIG. 2 is an HPLC chromatogram showing the elution of the combination mixture of human A chain S-sulfonate and human [10-Aspartic acid] B chain S-sulfonate. Panel A shows the initial chromatographic separation. Panel B depicts the rechromatography of the material in the peak eluting at 32.32 min shown in Panel A.

DESCRIPTION OF THE INVENTION

Figure 4:
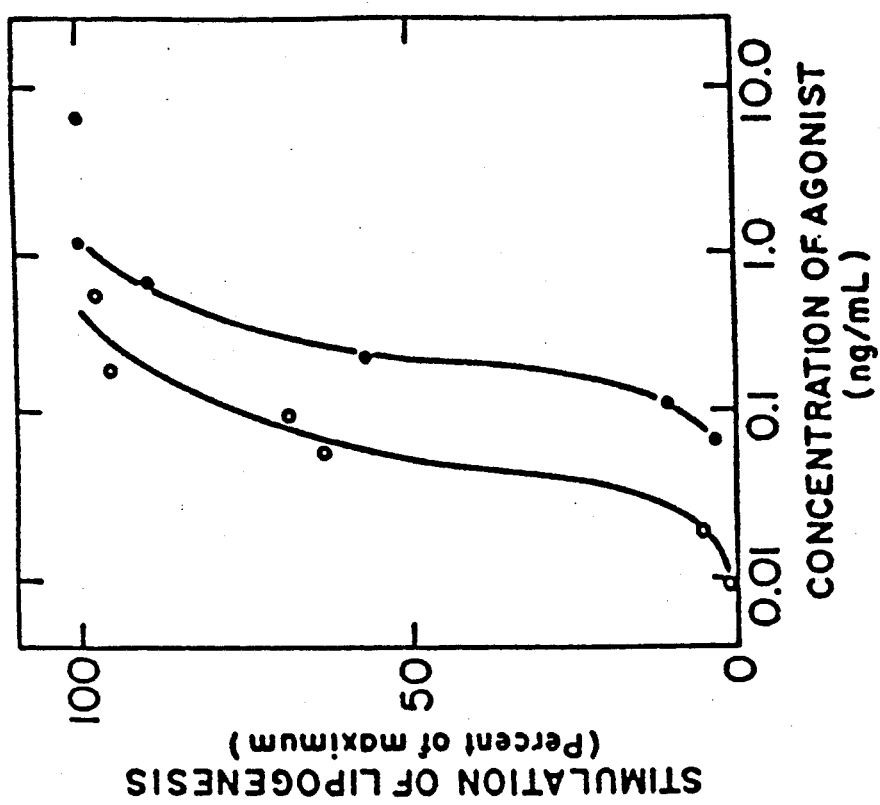
FIG. 4 is a graph showing the effect of [10-Aspartic acid-B] human insulin and bovine insulin on the stimulation of lipogenesis in rat adipocytes.

The present invention provides a superactive insulin analogue [10-Aspartic acid-B] human insulin of the formula

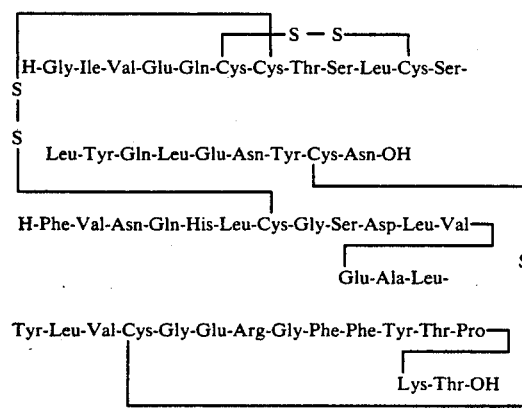

The term insulin analogue refers to a protein which has the basic A chain and B chain structure of human (and other species of) insulin and contains all of the half cysteine residues in the same position as present in native insulin. Thus, insulin analogues retain the disulfide bridge arrangement of natural insulins. Useful insulin analogues can differ from native insulins by the addition, deletion, substitution or modification of one or more amino acids in one or both chains of the molecule, but must retain at least some portion of insulin potency. See e.g. Katsoyannis, Treatment of Early Diabetics (1979), pp. 319–327, Plenum Publ. Corp.; Blondell, Adv. Prot. Chem. (1972), vol. 26, pp. 330–362.

The insulin analogue of the invention which differs from human insulin solely by the substitution of aspartic acid for histidine at position 10 of the B chain, was unexpectedly found to have greater potency than natural insulins, especially those used in diabetes therapy.

[10-Aspartic acid-B] human insulin can be produced by any of a variety of techniques known to those skilled in the art. For example, the component A and B chains of the insulin analogue can be synthesized by any of the known peptide systhesis techniques, including solid phase peptide synthesis techniques and solution techniques, e.g. fragment condensation. See, e.g. Erickson and Merrifield, The Proteins (1976), vol. 2, chapter 3, Academic Press, New York; Blake et al. Proc. Natl. Acad. Sci. (1983), vol. 80, pp. 1556–1559 for a discussion of peptide synthesis techniques. The [10-Aspartic acid-B] human insulin can also be prepared by combining human or porcine A chains, isolated following reduction or oxidative sulfitolysis of intact pancreatic or recombinant insulin, with a [10-Aspartic acid] B chain prepared by peptide synthetic techniques or recombinant DNA methods. It is known that the A chains of porcine and human insulins are identical to each other in amino acid sequence, so that porcine A chain can readily substitute for human A chains in any method of producing [10-Aspartic acid-B] human insulin.

Recombinant DNA methods for producing the human insulin B chain having aspartic acid at position 10 include, but are not limited to, cloning and expression of an in vitro synthesized DNA which codes for such a B chain amino acid sequence. Alternatively, an organism, such as bacteria, which expresses human insulin B chain could be induced to produce [10Aspartic acid] B chain by any of the techniques of in vitro site-directed mutagenesis. See e.g. Smith, Ann. Rev. Genet. (1985), vol. 19, pp. 423–463; Botstein et al. Science (1985), vol. 229, pp. 1193–1201.

In general, to prepare [10-Aspartic acid-B] human insulin, human or porcine insulin A chains, obtained by any known technique are combined with [10 Aspartic acid] human B chains prepared by any convenient technique. The A and [10-Aspartic acid] B chains are preferably in their stabilized S-sulfonated forms which can then be recombined by known procedures to form the intact active human insulin analogue. Known recombination techniques are taught by U.S. Pat. No. 3,420,810 to Katsoyannis and U.S. Pat. No. 4,421,685 to Chance et al. For example, U.S. Pat. No. 4,421,685 provides a single step process for forming an insulin which involves bringing together an S-sulfonated A chain and S-sulfonated B chain in the presence of a thiol reducing agent, such as dithiothreitol or cysteine, in an aqueous medium. The conditions for recombination include (1) a pH of about 8 to 12, (2) a total protein concentration of about 0.1 to 50 mg/ml, and (3) a thiol reducing agent in a concentration which produces about 0.4 to 2.5 SH groups per each - S-SO$_3$ group present in the total A and B chain S-sulfonates present in the mixture. The formation of [10-Aspartic acid-B] human insulin occurs by maintaining the reaction at a temperature of about 0° to 25° C. in an environment which provides a source of oxygen to allow the formation of the insulin S-S bonds.

Once the recombination reaction has been completed, the insulin analogue can be isolated and assayed for purity and activity by a variety of techniques known to those skilled in the art. Commonly employed techniques for purification of insulin and insulin analogues are chromatographic techniques, such as high performance liquid chromatography (HPLC), gel filtration and ion-exchange chromatography. Purity of the product can be determined by a variety of techniques including inter alia HPLC, polyacrylamide gelelectrophoresis, amino acid analysis and amino acid sequencing.

Although insulin analogues, in general, maintain some residual insulin activity, the potency of such analogues is usually only a fraction of that of natural insulins. The potency of human, bovine and porcine insulins in USP standards is about 25–26 IU (international units) per mg protein. Surprisingly [10-Aspartic acid-B] human insulin was determined to be about 4–6 times more potent than natural insulins in assays which measure the potency of insulin. Standard assays for measuring insulin potency include inter alia (1) insulin radioreceptorassays, in which the relative potency of an insulin is defined as the ratio of insulin to insulin analogue required to displace 50% of $^{125}$I-insulin specifically bound to insulin receptors present on cell membranes, e.g. a rat liver plasma membrane fraction; (2) lipogenesis assays, performed e.g. with rat adipocytes, in which relative insulin potency is defined as the ratio of insulin to insulin analogue required to achieve 50% of the maximum conversion of [3-$^{3}$H] glucose into organic-extractable material (i.e. lipids); (3) glucose oxidation assays in isolated fat cells in which the relative potency of the insulin analogue is defined as the ratio of insulin to insulin analogue to achieve 50% of the maximum conversion of glucose-1-[$^{14}$C] into [$^{14}$CO$_2$]; (4) insulin radioimmunoassays which can determine the immunogenicity of insulin analogues by measuring the effectiveness by which insulin or an insulin analogue competes with $^{125}$I-insulin in binding to specific anti-insulin antibodies; and (5) other assays which measure the binding of insulin or an insulin analogue to cells, such as cultured lymphocytes, known to possess specific insulin receptors. In standard assays to measure relative insulin potency, e.g. assays (1), (2) and (5) listed above, [10-Aspartic acid-B] human insulin was determined to be about 4–6 times more active or potent than natural insulins.

The human insulin analogue of the invention may also be formulated into pharmaceutical compositions for administration to diabetic patients. The pharmaceutical compositions comprise [10-Aspartic acid-B] human insulin in an amount which is therapeutically effective in promoting the attainment of hormonal homeostasis in the diabetic patient together with a pharmaceutically acceptable carrier. As with all insulin preparations for treatment of diabetes, adequate therapeutic amounts of the active compound to achieve hormonal homeostasis in individual patients must be determined. Factors to be considered include the severity of the diabetic condition and the route of administration of the composition. Ultimately the particular physician treating the diabetic patient has discretion in the amount of the pharmaceutical composition and route of administration. Natural insulins are generally given to a patient in a therapeutic dosage to afford about 0.02 to about 5 units of human insulin activity per kilogram body weight per day. See e.g. U.S. Pat. No. 4,652,547.

Because the insulin analogue is more potent than natural insulin in vitro, it is believed that the therapeutic amount of [10-Aspartic acid-B] human insulin required to achieve homestasis in diabetic patients may be less than the therapeutic amount of natural insulins now used to treat diabetes. In addition, another important advantage of this insulin analogue is faster clearnace from the blood of diabetic patents. It is known that insulin clearance from the blood is mediated by the insulin receptor on cells. Since [10-Aspartic acid-B] human insulin has been shown to bind to the insulin receptor about five times more tightly than natural insulins, it is believed that this insulin analogue will be cleared from the blood of patients at a faster rate than natural insulins. As a consequence, it is believed that vascular toxicity associated with the growthpromoting effects of circulating insulin may be lessened by the use of [10-aspartic acid-B] human insulin in treatment for diabetics.

Pharmaceutical compositions containing a therapeutically effective amount of [10-Aspartic acid-B] human insulin may be administered parenterally to a diabetic patient in need of insulin treatment. Preferably the composition is administered intramuscularly, subcutaneously or intravenously. The composition may also be adminstered to the patient by nasal spray. Alternatively, for long-term controlled homeostasis, the composition may be incorporated into an implantable pump for administration to the patient. Such implantable devices which provide a controlled dosage of drug to a patient over a long period of time are known in the art. The composition additionally comprises a pharmaceutically acceptable carrier which must not be deleterious to the recipient patient. The carrier must also not have any adverse effect on the active component of the composition, i.e., [10-Aspartic acid-B] human insulin. Suitable carriers and other additives for pharmaceutical compositions which contain therapeutically effective amounts of [10-Aspartic acid-B] human insulin as the active component may be found in U.S. Pat. No. 4,652,547 which provides for insulincontaining compositions.

The invention is further illustrated by the following specific examples which are not intended in any way to limit the scope of the invention.

EXAMPLE 1

Synthesis of [10-Aspartic acid-B] Human Insulin

[10-Aspartic acid-B] human insulin was synthesized by peptide synthesis using fragment condensation techniques. (See, for example, Blake et al., Proc. Natl. Acad. Sci. (1983), vol. 80, pp. 1556–1559 for general techniques.) The honogeneity of all intermediate peptide derivatives was ascertained by thin layer chromatography on 6060 silica gel (Eastman Chromatogram sheet). The solvent systems used to develop the chromatograms were chloroform-methanol-water (45:10:1; 89:10:1; and 200:75:13).

[10-Aspartic acid-B] human insulin was prepared by combining the S-sulfonated form of human insulin A chain with the synthetic S-sulfonated derivative of human insulin [10-Aspartic acid] B chain in the presence of dithiothreitol as provided in U.S. Pat. No. 4,421,685 to Chance et al. The S-sulfonated human A chain, which is identical with the respective chain of porcine insulin (Nicol et al, Nature (1960), vol. 181, pp.

483–485), was prepared by oxidative sulfitolysis of porcine insulin and separation of the resulting S-sulfonated A and B chains by column chromatography as described by Katsoyannis et al., Biochemistry (1967), vol. 6, pp. 2635–2624. The synthesis of the S-sulfonated human [10-Aspartic acid] B chain was patterned after that of S-Sulfonated natural human B chain as described by Schwartz and Katsoyannis, J. Chem. Soc. Perkin Trans. I (1973), pp. 2894–2901. The C-terminal hexadecapeptide (sequence $B^{15}$–$B^{30}$) was coupled with the adjacent hexapeptide (sequence $B^9$–$B^{14}$) to produce the C-terminal docosapeptide (sequence $B^9$–$B^{30}$). This in turn was coupled with the N-terminal octapeptide (sequence $B^1$–$B^8$) to yield a protected B chain analogue which, upon exposure to liquid hydrogen fluoride and oxidative sulfitolysis of the resulting sulfhydryl derivative, afforded the S-sulfonated form of the [10-Aspartic acid] B chain.

Table I provides some of the compounds and amino acid blocking groups used in the synthesis of the peptides and gives the abbreviations relating thereto.

TABLE I

| Compound | Abbreviation |
| --- | --- |
| benzyl | Bzl |
| tertiary-butoxycarbonyl | Boc |
| tertiary-butyl | $Bu^t$ |
| cyclohexyl | cHex |
| dicyclohexylamine | DCHA |
| dimethylformamide | DMF |
| dimethylsulfoxide | DMSO |
| diphenylmethyl | DPM |
| N,N′-dicyclohexlycarbodimide | DCC |
| 1-hydroxybenzotriazole | HOBT |
| benzyloxycarbonyl | Z |

A. Synthesis of S-Sulfonated [10-Aspartic acid]B Chains

Z.Glu(cHex).OH,DCHA (Compound I)

This compound was prepared from the respective Boc-derivative (Peninsula Laboratories) by deblocking with trifluoroacetic acid and carbobenzoxylation of the ensuing product. The resulting derivative was crystallized from ether as the dicyclohexylamine salt; mp 131°–132° C. Anal. Calcd for $C_{31}H_{48}N_2O_6$: C,86.4; H, 8.88; N, 5.4. Found: C, 68.3; H, 9.11; N, 5.1.

Z.Glu(cHex)-Ala.OBu$^t$ (Compound II)

Compound I (9.8 g) was partitioned between 0.2N $H_2SO_4$ and ethyl acetate and the organic layer was separated, washed with water, dried ($MgSO_4$) and concentrated to dryness. To a solution of the residue in DMF (30 ml) cooled to 0° C., H.Ala.OBu$^t$ [prepared from Z.Ala.OBu$^t$ (5.6 g) as described by Schwartz and Katsoyannis, supra] was added followed by HOBT (2.3 g) and DCC (3.7 g). After 24 hr at room temperature, the urea by-product was filtered off and the filtrate was diluted with ethyl acetate (500 ml) and washed successively with 1M $NaHCO_3$, water, 0.2N HCl and water, dried and concentrated, under reduced pressure, to dryness. The product was obtained as an oil [8 g (90%)] which was homogeneous on thin-layer chromatography and was used in the synthesis of the compound III without any further characterization.

Z.Val-Glu(cHex)-Ala.OBu$^t$ (Compound III)

Compound II (8 g) in methanol (150 ml) was hydrogenated over 10% Pd/C catalyst (2 g) for 3 hr. The catalyst was filtered off and the filtrate was concentrated, under reduced pressure, to dryness. The residue was mixed with an activation mixture of Z.Val.OH (4.1 g), HOBT (2.7 g) and DCC (3.3 g) in DMF (30 ml) (activated for 30 min at room temperature before addition of the amino component). After 24 hr the product was isolated in the same manner as described for compound II; oil, 8.7 g (85%). This material was homogeneous on thin-layer chromatography and was used in the following synthetic step without further characterization.

Z.Leu-Val-Glu (cHex)-Ala.OBu$^t$ (Compound IV)

Compound III (8 g) was hydrogenated as described above and the resulting oily residue was dissolved in DMF (30 ml). To this solution Z-leucine p-nitrophenyl ester (5.5 g) and HOBT (1.8 g) were added. After 48 hr, the mixture was diluted with ethyl acetate (250 ml), washed successively with 0.5N $NH_4OH$, water, 0.2N HCl and water, dried ($MgSO_4$) and concentrated to dryness in vacuo. The residue was crystallized from 95% ethanol: wt 8.4 g (88%); mp 190°–194°; $[\alpha]_D^{26}$ −20.3° (c 1, DMF). Anal. Calcd for $C_{37}H_{58}N_4O_9$: C, 63.2; H, 8.31; N, 8.0. Found: C, 62.9; H, 8.37; N, 8.1.

Boc.Asp(cHex)-Leu-Val-Glu(cHex)-Ala.OBu$^t$ (Compound V)

Compound IV (1.5 g) was hydrogenated as previously described and the residue was added to an activation mixture of Boc.Asp(cHex).OH (Peninsula Laboratories) (0.8 g), HOBT (0.34 g) and DCC (0.52 g) in DMF (10 ml) (activated for 30 min at room temperature before addition of the amino component). After 24 hr the reaction mixture was processed as described for Compound II, and the product was purified by reprecipitation from ethyl acetate-petroleum ether; wt 1.5 g (85%); mp 203°–205°; $[\alpha]_D^{26}$ −8.9° (c 1, DMF). Anal. Calcd for $C_{44}H_{75}N_5O_{12}$: C, 61.0; H, 8.72; N, 8.1. Found: C, 60.7; H, 8.56; N, 7.8.

Boc.Ser(Bzl)-Asp(cHex)-Leu-Val-Glu(cHex)-Ala.OH (Compound VI)

A solution of compound V (1 g) in trifluoroacetic acid (10 ml) was stored at room temperature for 2 hr and then concentrated to dryness in vacuo and the residue triturated with cold ether. The solid deblocked pentapeptide trifluoroacetic acid salt formed was filtered and dried over KOH. An activation mixture of Boc.-Ser(Bzl).OH (1.2 g), HOBT (0.5 g) and DCC (0.6 g) in DMF (10 ml) was prepared and after 30 min incubation, the mixture was filtered into a solution of the pentapeptide trifluoroacetic acid salt in DMSO (10 ml) containing N-methylmorpholine (0.13 ml). After 24 hr the reaction mixture was diluted with cold water (100 ml) and the precipitated product was filtered off, dried and reprecipitated from ethyl acetate-petroleum ether: wt 0.9 g (90%); mp 200°–203°; $[\alpha]_D^{26}$ −17.8° (c 1, DMF). Anal. Calcd for $C_{50}H_{78}N_6O_{14}$: C, 60.8; H, 7.96; N, 8.5. Found: C, 61.4; H, 8.25; N, 8.7. Amino acid ratios after acid hydrolysis: $Asp_{1.0}Ser_{0.8}Glu_{1.0}Ala_{1.0}Val_{1.1}Leu_{1.0}$.

Boc.Ser(Bzl)-Asp(cHex)-Leu-Val-Glu(cHex)-Ala-Leu-Tyr(Bzl)-Leu-Val-Cys(Dpm)-Gly-Glu(Bzl)-Arg($NO_2$)-Gly-Phe-Phe-Tyr(Bzl)-Thr-Pro-Lys(Z)-Thr(Bzl).OBzl (Compound VII)

A suspension of the free base of the partially protected hexadecapeptide (sequence $B^{15}$–$B^{30}$) of human insulin B chain (400 mg) prepared according to Schwartz et al., Int. J. Pept. Protein Res. (1981), vol. 17, pp. 243–255, compound VI (494 mg) and HOBT (80 mg) was stirred until solution occurred. This solution, after the addition of DCC (100 mg), was stirred at 4° C. for 48 hr and then diluted with 95% ethanol (150 ml). The precipitated docosapeptide (sequence $B^9$–$B^{30}$) was filtered off, washed with 95% ethanol and dried: wt 450 mg (88%). Amino acid analysis after acid hydrolysis gave the following composition expressed in molar ratios: $Asp_{1.1}Thr_{2.0}Ser_{1.0}Glu_{2.1}Pro_{1.0}Gly_{2.2}Ala_{0.9}Val_{1.9}Leu_{2.9}Tyr_{1.9}Phe_{2.0}Lys_{1.1}Arg_{0.7}$ (Cys was not determined).

H.Phe-Val-Asn-Gln-His-Leu-Cys(SO₃)-Gly-Ser-Asp-Leu-Val-Glu-Ala-Leu-Tyr-Leu-Val-Cys(SO₃)-Gly-Glu-Arg-Gly-Phe-Phe-Tyr-Thr-Pro-Lys-Thr.OH (Human Insulin [10-Aspartic Acid] B Chain S-sulfonate) (Compound VIII)

A solution of compound VII (400 mg) in a mixture of trifluoroacetic acid-acetic acid (7:3; v/v) (10 ml) was stored at room temperature for 1 hr and then diluted with ether. The precipitated trifluoroacetic acid salt of the docosapeptide was filtered off, washed with ether and dried. A solution of this product in N-methylpyrrolidone (6 ml) and DMF (6 ml) containing triethylamine (0.1 ml) was diluted with ether and dried. This product and Boc.Phe-Val-Asn-Gln-His-Leu-Cys(Dpm)-Gly.OH, prepared according to Schwartz and Katsoyannis, J. Chem. Soc. Perkin Trans. I (1973), pp. 2894–2901, (500 mg) were dissolved in a mixture of DMF (5 ml) and DMSO (5 ml) containing HOBT (90 mg) and then DCC (100 mg) was added. After 48 hr at room temperature, the mixture was poured into cold water (250 ml) containing 1N NH₄OH (5 ml) and the precipitated protected triacontapeptide was filtered off, washed (water, 50% methanol and methanol), dried and reprecipitated from DMF-methanol: wt 400 mg (90%).

This product was converted to the S-sulfonated [10-Aspartic acid]B chain by deblocking with liquid hydrogen fluoride followed by oxidative sulfitolysis as described by Schwartz and Katsoyannis, supra, for the synthesis of human insulin B chain S-sulfonate. The protected triacontapeptide (200 mg) was treated with anhydrous liquid hydrogen fluoride (9 ml) containing m-cresol (1 ml) at 0° C. for 1 hr. The hydrogen fluoride was then removed and the residue was triturated successively with ethyl acetate and petroleum ether. To a solution of this product in 8M guanidine hydrochloride (20 ml), buffered with 0.1M Tris-HCl (pH 8.8), sodium sulfite (700 mg) and sodium tetrathionate (500 mg) were added. After 3 hr at room temperature the reaction mixture was placed in dialysis tubing, e.g. Spectrapor® membrane tubing No. 3, dialyzed against four changes of distilled water (4 l each) at 4° C. for 24 hr, and lyophilized.

For purification the lyophilized material was dissolved in 3 ml of urea acetate buffer (0.04M acetate-8M urea, pH 4.0) and applied to a CM-cellulose column (2.5×40 cm) which was eluted isocratically with the same buffer. See e.g., Katsoyannis et al, Biochemistry (1967), vol. 6 pp. 2635–2642. The column effluent was monitored with a spectrophotometer (ISCO Model U-5A) which gave the elution pattern shown in FIG. 1. The eluate under the main peak (125–168 ml) was collected, dialyzed as described above, and upon lyophilization the S-sulfonated [10-Aspartic acid]B chain was obtained as a white powder: wt 22 mg. Amino acid analysis of the purified chain, after acid hydrolysis gave the following composition expressed in molar ratios, in agreement with the theoretically expected values: $Asp_{2.1}Thr_{2.1}Ser_{1.1}Pro_{1.1}Glu_{3.0}Gly_{2.9}Ala_{1.0}Val_{3.0}Leu_{3.8}Tyr_{1.8}Phe_{2.9}Lys_{1.1}His_{1.0}Arg_{0.9}$ (Cys was not determined).

B. Synthesis and Isolation of [10-Aspartic acid-B] Human Insulin

To a solution of S-sulfonated human (porcine) A chain (40 mg) and S-sulfonated human [10-Aspartic acid-B] chain (20 mg) in 10 ml of 0.1M glycine buffer, pH 10.6, cooled to 4° C., dithiothreitol (7 mg) was added. After 24 hr at 4° C. the mixture was diluted with acetic acid (1 ml) and the resulting precipitate was removed by centrifugation (International Centrifuge, Model HN; 3000 rpm). The supernatant, containing the active material, was passed through a 0.45 μ cellulose acetate filter (Sartorius) and subjected to reversed-phase HPLC using a Vydac® 218 TP column (0.45×25 cm) connected to an LKB liquid chromatography system. Batches (ca 5 mg of protein each) were chromatographed at a flow rate of 0.5 ml/min with a 10 to 50% linear gradient of 2-propanol in 0.1% trifluoroacetic acid over 70 min. The chromatographic pattern is shown in FIG. 2A. Biological assays as described in Examples 2-4 indicated that only the material that eluted at ca 32.3 min had substantial insulin activity. Under these same chromatographic conditions bovine insulin was eluted at 30 min. The fraction containing the active material was concentrated and rechromatographed using the same column and a 20 to 35% linear gradient of 2-propanol in 0.1% trifluoroacetic acid at a flow rate of 0.5 ml/min over 85 min. The elution pattern is shown in FIG. 2B. The fraction containing the active material, eluting at ca 47.2 min, was collected, concentrated and used for the biological studies described in Examples 2-4. Under these same chromatographic conditions bovine insulin was eluted at ca 38 min. From the combination mixture of A and B chains described above, 2 mg of highly purified product was obtained. Amino acid analysis of the purified synthetic material, after acid hydrolysis, gave the following composition, expressed in molar ratios, in good agreement with the theoretically expected values: $Asp_{4.0}Thr_{2.8}Ser_{3.1}Pro_{1.0}Glu_{7.0}Gly_{4.0}Ala_{1.1}Val_{3.4}Ile_{1.4}Leu_{5.9}Tyr_{3.6}Phe_{2.9}Lys_{1.1}His_{1.0}Arg_{1.0}$ (Cys was not determined).

EXAMPLE 2

Analysis of [10-Aspartic acid-B] Human Insulin Potency by Insulin Receptor Binding Assay Receptor binding assays using rat liver plasma membranes were performed as described by Kitagawa et al., Biochemistry (1984), vol. 23, pp. 1405–1413. Rat liver plasma membranes were prepared as described by Horvat et al., Biochim. Biophys. Acta (1975), vol. 382, pp. 609–620.

Briefly, triplicate 0.2-ml incubations contained $^{125}I$-insulin, $3\times10^{-10}M$, unlabeled insulin or [10-Aspartic acid-B] human insulin prepared as in Example 1, and plasma membranes (20–40 μg of protein) in 0.1M sodium phosphate, pH 7.4, containing 0.6% fraction V bovine serum albumin. Following incubation for 45 min at 24° C., the mixtures were diluted with 2.0 ml of ice cold 0.1M sodium phosphate, pH 7.4, containing 0.1% fraction V bovine serum albumin and immediately filtered through cellulose-acetate filters. The filters were washed twice with the ice cold buffer, dried, and then radioactivity was counted in a scintillation counter using Filtron-X®. Nonspecific binding, defined as radioactivity remaining on the filters when the incubations contained $1\times10^{-5}M$ unlabeled insulin, was subtracted from all values. Relative potency was obtained as the concentration ratio of unlabeled insulin to [10-Aspartic acid-B] human insulin required to inhibit 50% of the specific binding of $^{125}$I-insulin to the receptor preparation.

Figure 3:
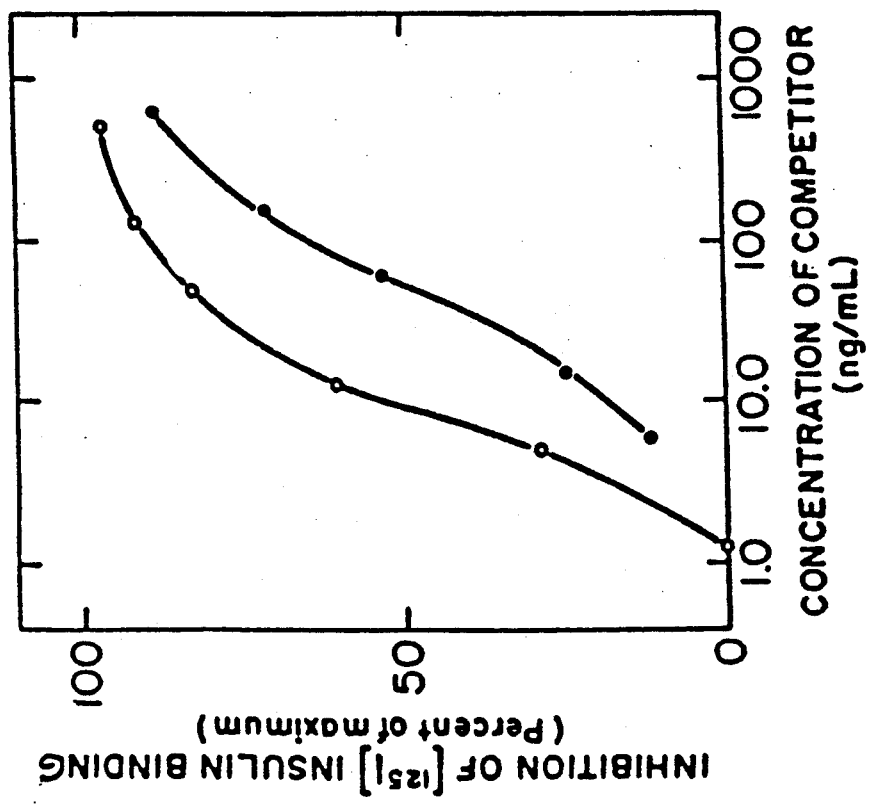
FIG. 3 is a graph showing the competitive inhibition of $^{125}$I-insulin binding to rat liver plasma insulin receptors by [10-Aspartic acid-B] human insulin (o) and bovine insulin (•).

FIG. 3 depicts the ability of bovine insulin (•) and [10-Aspartic acid-B] human insulin (o) to compete with $^{125}$I-insulin in binding to insulin receptors in rat liver plasma membranes. Inhibition of binding, expressed as percent of maximum, was plotted as a function of competitor concentration. The data points shown in FIG. 3 represent the mean of triplicate determinations in a representative assay which was performed four times. The maximum binding in these assays amounted to 8.2% of the input radioactivity.

As can be seen from FIG. 3, the dose response curves of [10-Aspartic acid-B] human insulin and bovine insulin were essentially parallel. The potency of [10-Aspartic acid-B] human insulin calculated as provided above, however, was about 534±146% relative to bovine insulin.

EXAMPLE 3

Analysis of [10-Aspartic acid-B] Human Insulin Potency by Lipogenesis Assays Lipogenesis assays to measure the potency of the insulin analogue were performed as described by Kitagawa et al., supra. The assays measured the ability of the insulin analogue as compared to bovine insulin to convert, [3-$^3$H] glucose into lipids.

Adipocytes were prepared by incubating epididymal and perirenal fat pads obtained from male rats weighing 200–300 g with 1.0 mg/ml collagenase for 60 min at 37° C., followed by filtration through gauze and then through fine-mesh silk. Cells were washed twice by flotation in a clinical centrifuge before suspension for use. The incubation medium was Krebs-Ringer bicarbonate containing half the recommended calcium, 0.5 mM glucose, and 3% fatty acid free bovine serum albumin, with 95% $O_2$-5% $CO_2$ as the gas phase. Triplicate lipogenesis incubations contained 1.0 ml of adipocyte suspension (20–40 mg dry wt cells) and bovine insulin or [10-Aspartic acid-B] human insulin, prepared as in Example 1. Cells were preincubated for 45 min at 37° C. before the addition of [3-$^3$H] glucose. Incubation was continued for 60 min and stopped by the addition of 0.2 ml of 5N $H_2SO_4$ and 0.2 ml of corn oil to aid in the extraction of lipids. Samples were extracted with 10 ml of Soluscint-0 ® for 30 min at room temperature before counting the radioactivity in a scintillation counter. Under these conditions, [3-$^3$H] glucose was not extracted into the organic phase containing the scintillation fluors and was essentially uncounted. Zero and 100% stimulation of lipogenesis were defined as radioactivity observed in the absence and presence, respectively, of $9.1 \times 10^{-10}$M insulin (5.5 ng/ml). Relative potency was obtained as the concentration ratio of insulin to [10-Aspartic acid-B] human insulin required to produce 50% of the maximum stimulation of lipogenesis.

FIG. 4 shows the stimulation of [3-$^3$H] glucose into organic-extractable material (i.e., lipids) in isolated rat adipocytes by [10-Aspartic acid-B] human insulin (o) prepared as in Example 1 and bovine insulin (•). Stimulation, expressed as percent of maximum, was plotted as a function of the agonist concentration. The data points represent the mean of triplicate determinations in representative assays performed four times. In the assays, 0% and 100% stimulation refer to 0.3 and 3.5 nmol glucose per mg cells per hr, respectively.

The data represented in FIG. 4 shows that [10-Aspartic acid-B] human insulin was a full agonist in the assays, reaching the same maximum stimulation of lipogenesis as the natural bovine insulin. The relative potency of [10-Aspartic acid-B] human insulin, however, was calculated to be 435±144% relative to the bovine insulin.

The potency values calculated for [10-Aspartic acid-B] human insulin in the receptor binding assays of Example 2 and the present lipogenesis assays were determined to be not statistically different (0.4>p>0.3 by Student's t-test).

It is, thus, readily apparent that [10-Aspartic acid-B] human insulin, is a superactive insulin displaying in vitro potency about five times greater than natural insulin.

EXAMPLE 4

Radioimmunoassay Analysis of [10-Aspartic acid-B] Human Insulin

Radioimmunoassay analyses as described by Kitagawa et al., supra, were carried out to assess whether [10-Asparticacid-B] human insulin was immunologically distinguishable from natural insulin.

Guinea pig antiserum to porcine insulin and goat anti-guinea pig-$\gamma$ globulin were used at a 1:25 dilution in assay buffer (sodium phosphate, 0.04M, pH 7.6, containing 0.154M NaCl, 0.1% gelatin, and 0.01% thimerosal). Duplicate assay tubes contained 0.1 ml of anti-insulin antiserum, 0.072 ng of $^{125}$I-insulin, and bovine insulin (0.06–0.36 ng) or [10-Aspartic acid-B] human insulin prepared as in Example 1 (1–4.0 ng) in a total volume of 0.8 ml. After incubation at room temperature overnight, 0.2 ml of the precipitating antibody (goat anti-guinea pig-$\gamma$ globulin) was added, and the tubes were further incubated overnight at room temperature. Immune precipitates were collected on cellulose-acetate filters and washed with two successive 1.0 mL portions of ice-cold assay buffer. Filters were dried and radioactivity was counted in a scintillation counter in Filtron-X ®. Straight-line plots of $C_o/C_i$ were constructed by linear regression analysis as described by Hales et al., Biochem. J. (1963), vol. 88, pp. 137–146, and the potency of [10-Aspartic acid-B] human insulin relative to bovine insulin was obtained as the ratio of the slopes of such plots.

Synthetic [10-Aspartic acid-B] human insulin exhibited approximately equal potency to bovine or porcine insulin in the radioimmunoassays. This result indicated that the substitution of aspartic acid for histidine at position $B^{10}$ did not have a significant effect on the immunogenic determinants of the molecule.

DISCUSSION OF THE EXAMPLES

Prior X-Ray analyses have indicated that histidine at position $B^{10}$ resides at the surface of the insulin monomer and is important in the formation of zinc insulin hexamers. See, e.g. Blundell et al., Adv. Prot. Chem. (1972), vol. 26, pp. 279–402. Previous studies have shown that replacement of histidine at position $B^{10}$ with leucine, lysine, or asparagine produced synthetic insulin analogues displaying reduced biological potency, ca 14 to 45%, relative to the natural hormone. See, Schwartz et al., J. Chem. Res. (S), pp. 220–221, J. Chem. Res. (M), pp. 2453–2469 (1977); Schwartz et al., J. Prot. Chem. (1982), vol. 1, pp. 177–189; Burke et al., Int. J. Protein Res. (1984), vol. 23, pp. 394–401. From these studies it had been concluded that hydrophilicity at $B^{10}$ per se was relatively unimportant in determining biological activity of insulin and the presence of a strongly basic amino acid residue at that position was deleterious. It had been further suggested that the ability to exist in either a protonated or unprotonated state near physiological pH, a property unique to a histidine residue, was believed to be a requirement at position $B^{10}$ for high biological activity. See, e.g., Burke et al., supra. [10-Aspartic acid-B] human insulin, which at physiological pH would have a negative charge at the $B^{10}$ position, however, was found to be several fold more active than natural insulin in in vitro experiments as shown in the Examples.

The superactivity of [10-Aspartic acid-B] human insulin apparently results from stronger binding to the insulin receptor. It is believed that the stronger binding of the analogue to the receptor may be due to a change in conformation of the analogue more favorable for binding to the receptor, resulting from intramolecular interactions involving the negative charge at position $B^{10}$ (e.g., a salt bridge). Alternatively, the stronger binding may result from a direct interaction with a complementary surface on the receptor containing a positive charge. In reversed-phase HPLC, as shown in FIG. 2, [10-Aspartic acid-B] human insulin, under two chromatographic conditions, eluted significantly later than natural insulin. This behavior indicated that the synthetic analogue was a more apolar molecule. The large difference in polarity exhibited between natural insulin and [10-Aspartic acid-B] human insulin cannot be ascribed to the substitution of one hydrophilic residue for another. It is believed that the most reasonable explanation for the difference in polarity is that it reflects a change in conformation which is believed to result in stronger binding of the analogue to the insulin receptor.

We claim:

1. A superactive insulin analogue of the formula

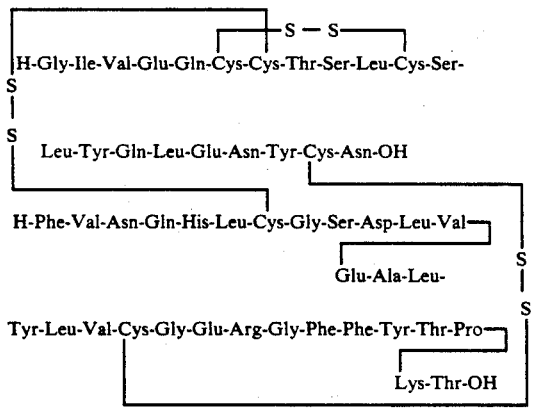

2. A pharmaceutical composition for the treatment of diabetes in a patient in need of such treatment comprising a therapeutically effective amount of a superactive human insulin analogue of the formula

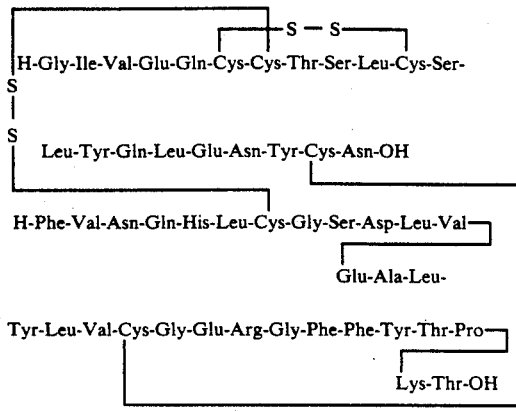

together with a pharmaceutically acceptable carrier.

3. A method of treating diabetes in a patient in need of such treatment comprising administering to the patient a therapeutically effective amount of a superactive insulin analogue of the formula

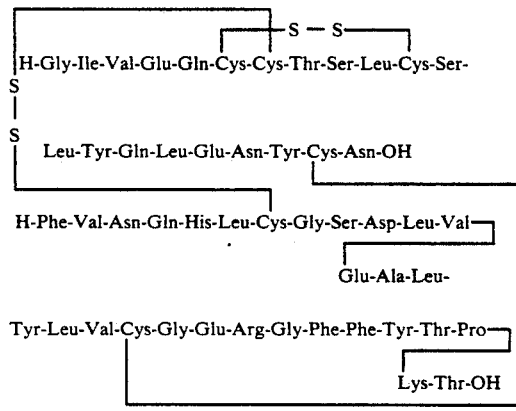

together with a pharmaceutically acceptable carrier.

4. Method according to claim 3 in which the superactive insulin analogue is administered intramuscularly.

5. Method according to claim 4 in which the superactive insulin analogue is administered subcutaneously.

6. Method according to claim 5 in which the superactive insulin analogue is administered intravenously.

7. Method according to claim 6 in which the superactive insulin analogue is administered by an implantable pump.

* * * * *

UNITED STATES PATENT AND TRADEMARK OFFICE
CERTIFICATE OF CORRECTION

PATENT NO. : 4992418  
DATED : February 12, 1991  
INVENTOR(S) : Katsoyannis et al.

Page 1 of 2

It is certified that error appears in the above-identified patent and that said Letters Patent is hereby corrected as shown below:

Column 1, line 5, insert -- This invention was made with government support under grant #DK-12925 awarded by the National Institutes of Health. The government has certain rights in the invention. --

Column 6, line 6, delete "homestasis" and substitute -- homeostasis -- therefor.

Column 6, line 10, delete "patents" and substitute -- patients -- therefor.

Column 6, line 55, delete "honogeneity" and substitute -- homogeneity -- therefor.

Column 7, line 5, delete "2624" and substitute -- 2642 -- therefor.

Column 9, line 53, delete "Biochemisry" and substitute -- Biochemistry -- therefor.

Column 14, line 49, delete "claim 4" and substitute -- claim 3 -- therefor.

Column 14, line 51, delete "claim 5" and substitute -- claim 3 -- therefor.

UNITED STATES PATENT AND TRADEMARK OFFICE
CERTIFICATE OF CORRECTION

PATENT NO. : 4,992,418

DATED : February 12, 1991

INVENTOR(S) : Panayotis G. Katsoyannis, et al.

It is certified that error appears in the above-identified patent and that said Letters Patent is hereby corrected as shown below:

Column 14, line 53, delete "claim 6" and insert --claim 3 --.

Signed and Sealed this

Fourth Day of May, 1993

Attest:

MICHAEL K. KIRK

Attesting Officer

Acting Commissioner of Patents and Trademarks